(12) United States Patent
Albrecht et al.

(10) Patent No.: US 9,232,963 B2
(45) Date of Patent: *Jan. 12, 2016

(54) TROCAR WITH RETENTION CANNULA

(71) Applicant: Applied Medical Resources Corporation, Rancho Santa Margarita, CA (US)

(72) Inventors: Jeremy J. Albrecht, Racho Santa Margarita, CA (US); Gary M. Johnson, Rancho Santa Margarita, CA (US); Matthew M. Becerra, Rancho Santa Margarita, CA (US); Travis King, Diamond Bar, CA (US); Donald L. Gadberry, Rancho Santa Margarita, CA (US); Isabel Simons, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/137,229

(22) Filed: Dec. 20, 2013

(65) Prior Publication Data

US 2014/0135585 A1 May 15, 2014

Related U.S. Application Data

(63) Continuation of application No. 13/460,993, filed on May 1, 2012, now Pat. No. 8,622,969, which is a continuation of application No. 12/903,006, filed on Oct. 12, 2010, now Pat. No. 8,167,843.

(60) Provisional application No. 61/366,010, filed on Jul. 20, 2010, provisional application No. 61/250,399, filed on Oct. 9, 2009.

(51) Int. Cl.
*A61B 17/34* (2006.01)
*A61B 17/02* (2006.01)

(52) U.S. Cl.
CPC ......... *A61B 17/3423* (2013.01); *A61B 17/0218* (2013.01); *A61B 17/3421* (2013.01); *A61B 2017/349* (2013.01); *A61B 2017/3484* (2013.01)

(58) Field of Classification Search
CPC ..................... A61B 17/3421; A61B 2017/349
See application file for complete search history.

(56) References Cited

U.S. PATENT DOCUMENTS

| 4,670,008 A | 6/1987 | Von Albertini |
| 5,258,003 A | 11/1993 | Ciaglia et al. |

(Continued)

FOREIGN PATENT DOCUMENTS

| DE | 197 18 086 | 11/1998 |
| WO | WO 97/14454 | 4/1997 |
| WO | WO 00/54678 | 9/2000 |

OTHER PUBLICATIONS

European Patent Office, The International Search Report and the Written Opinion of the International Searching Authority mailed Jan. 7, 2011 for International Application No. PCT/US2010/052356 entitled "Trocar With Retention Cannula".

(Continued)

*Primary Examiner* — Aarti B Berdichevsky
(74) *Attorney, Agent, or Firm* — John F. Heal

(57) ABSTRACT

A trocar comprises a retention cannula comprising an inverted or incised retention pattern disposed thereon. Embodiments of the incised cannula exhibit reduced tissue trauma compared with screw-threaded cannula, improved fixation and/or retention compared with an unthreaded cannula, and good sealing between the cannula and the incision.

17 Claims, 8 Drawing Sheets

(56) References Cited

U.S. PATENT DOCUMENTS

| | | | |
|---|---|---|---|
| 5,697,913 A | 12/1997 | Sierocuk et al. | |
| 6,210,376 B1* | 4/2001 | Grayson | 604/264 |
| 6,569,119 B1* | 5/2003 | Haberland et al. | 604/167.03 |
| 6,638,265 B1 | 10/2003 | Ternamian | |
| 7,608,062 B2* | 10/2009 | Sweeney | 604/264 |
| 7,608,097 B2* | 10/2009 | Kyle | 606/304 |
| 8,167,843 B2* | 5/2012 | Albrecht et al. | 604/164.04 |
| 8,622,969 B2* | 1/2014 | Albrecht et al. | 604/164.04 |
| 2006/0142779 A1 | 6/2006 | Arramon et al. | |
| 2006/0211992 A1 | 9/2006 | Prosek | |

OTHER PUBLICATIONS

The International Bureau of WIPO, International Preliminary Report on Patentability, for International Application No. PCT/US2010/052356, dated Apr. 11, 2012, entitled Trocar With Retention Cannula.

* cited by examiner

TROCAR WITH RETENTION CANNULA

CROSS REFERENCE TO RELATED APPLICATIONS

This application is a continuation of U.S. patent application Ser. No. 13/460,993, entitled "TROCAR WITH RETENTION CANNULA," filed May 1, 2012, currently pending, which is a continuation of U.S. patent application Ser. No. 12/903,006, entitled "TROCAR WITH RETENTION CANNULA," filed Oct. 12, 2010, which issued as U.S. Pat. No. 8,167,843, which claims the benefit of U.S. Provisional Patent Application No. 61/366,010, entitled "TROCAR WITH RETENTION CANNULA," filed Jul. 20, 2010, and U.S. Provisional Patent Application No. 61/250,399, entitled "TROCAR WITH RETENTION CANNULA," filed Oct. 9, 2009. These applications are incorporated by reference herein in their entireties.

BACKGROUND

1. Technical Field

This disclosure is generally related to surgical instruments, and more particularly, to a trocar comprising a retention cannula with an inverted or incised retention pattern disposed thereon.

2. Description of the Related Art

Laparoscopic procedures often use trocars to provide instrument access across a body wall into a body cavity, while protecting the incision against trauma from instrument manipulation. Trocars with unthreaded cannula exhibit reduced incision site trauma and smaller incision sizes compared with a trocar with a threaded cannula, at the expense of reduced retention force. Cannulae equipped with barbs reduce the likelihood of the cannula pulling out of the body wall mid-procedure; however, the cannula barbs do not prevent the cannula from migrating inward over the course of a procedure.

SUMMARY OF THE INVENTION

A trocar comprises a retention cannula comprising an inverted or incised retention pattern disposed thereon. Embodiments of the incised cannula exhibit reduced tissue trauma compared with screw-threaded cannula, improved fixation and/or retention compared with an unthreaded cannula, and good sealing between the cannula and the incision.

Some embodiments provide a trocar comprising: a retention cannula comprising: a proximal end, a distal end, and a longitudinal axis; a cannula wall defining a lumen extending between the proximal end and the distal end; a tip disposed at the distal end of the cannula, a cannula body between the proximal end of the cannula and the tip; and an inverted, tissue retention pattern extending into the wall of on the cannula body, wherein an outer diameter of the inverted pattern is not greater than an outer diameter of the cannula body; and a seal assembly coupled to the proximal end of the cannula.

In some embodiments, the inverted pattern comprises a thread root defining the outer diameter of the inverted pattern and a thread tip defining the outer diameter of the cannula body. In some embodiments, the inverted pattern comprises at least one of a fillet and a chamfer. In some embodiments, the thread root has a width, and the width of the thread root is not constant over the inverted pattern. In some embodiments, the inverted pattern comprises a first plurality of thread roots extending circumferentially about the cannula wall generally perpendicularly to the longitudinal axis of the trocar. In some embodiments, each of the first plurality of thread roots extends circumferentially about the cannula wall about an arced segment defining an angle less than 180 degrees. In some embodiments, the inverted pattern further comprises a second plurality of thread roots each having a retention segment extending circumferentially about the cannula wall generally perpendicularly to the longitudinal axis of the trocar, and a flow channel extending circumferentially about the cannula wall transverse to the longitudinal axis. In some embodiments, the retention segments are joined to adjacent flow channels such that the second plurality of thread roots defines a continuous channel. In some embodiments, each retention segment of the second plurality of thread roots is spaced from an adjacent retention segment by at least one of the thread roots of the first plurality of thread roots. In some embodiments, each retention segment of the second plurality of thread roots is spaced from an adjacent retention segment by one of the thread roots of the first plurality of thread roots.

In some embodiments of trocar, the inverted pattern comprises a continuous thread root having alternating retention segments extending circumferentially about the cannula wall generally perpendicularly to the longitudinal axis of the trocar and flow channels extending circumferentially about the cannula wall transverse to the longitudinal axis.

In some embodiments of trocar, the cannula wall has a region of relatively high thickness and wherein the inverted pattern is disposed in the region of relatively high thickness such that the inverted pattern comprises a thread root defining the outer diameter of the inverted pattern and a thread tip defining an outer diameter greater than the outer diameter of the cannula body.

In certain embodiments, a trocar is provided comprising a retention cannula and a seal assembly. The retention cannula comprises a tubular body, a tip, and a tissue retention channel. The tubular body has a proximal end, a distal end, a lumen extending between the proximal end and the distal end, an outer diameter, and a longitudinal axis. The tip is disposed at the distal end of the tubular body. The tissue retention channel extends radially into the tubular body and has a root surface with a diameter less than the diameter of the tubular body. The tissue retention channel comprises a first plurality of thread roots and a second plurality of thread roots. The first plurality of thread roots extends generally perpendicular to the longitudinal axis of the tubular body; and the second plurality of thread roots each has a retention segment extending generally perpendicular to the longitudinal axis of the tubular body and a flow channel extending generally transverse to the longitudinal axis of the tubular body. The seal assembly is coupled to the proximal end of the cannula.

In some embodiments of trocar, the second plurality of thread roots are continuous to define a continuous thread root.

In some embodiments of trocar, wherein each thread root of the first plurality of thread roots extends circumferentially around the tubular body about an arc segment of less than 180 degrees and each thread root of the first plurality of thread roots is positioned such that each thread root of the first plurality of thread roots is spaced apart from adjacent thread roots.

In some embodiments of trocar, each retention segment of the second plurality of thread roots is spaced from an adjacent retention segment by at least one of the thread roots of the first plurality of thread roots.

DETAILED DESCRIPTION OF CERTAIN EMBODIMENTS

Figure 1:
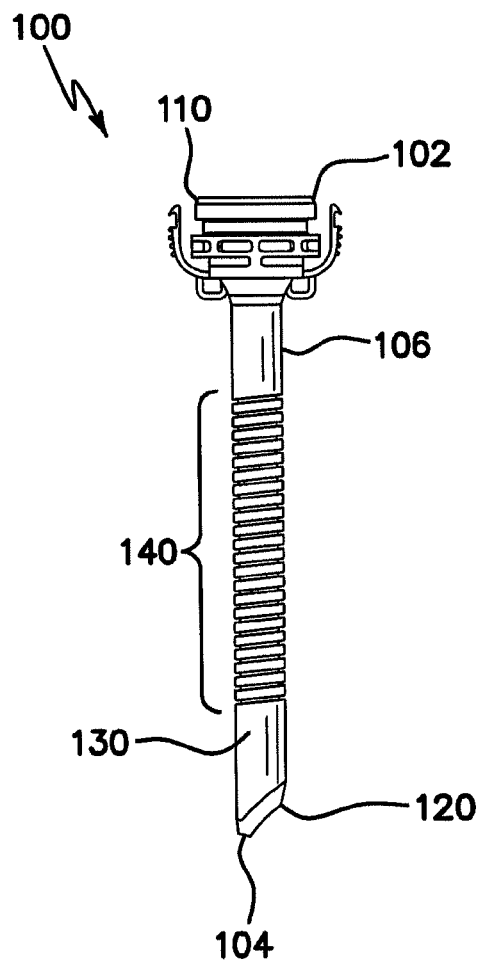
FIG. 1 is a side view of an embodiment of a cannula portion of a trocar comprising an inverted thread.

FIG. 1 is a side view of an embodiment of a cannula portion of a trocar. The retention cannula 100 comprises a proximal end 102, a distal end 104, a longitudinal axis, and a tubular wall 106 defining a lumen extending from the proximal end 102 to the distal end 104 of the cannula 100. A bell 110 disposed at the proximal end 102 is couplable to a trocar seal assembly (not illustrated). The distal end 104 terminates in an angled, beveled tip 120 in the illustrated embodiment. A generally cylindrical cannula body 130 extends between the bell 110 and the tip 120.

An inverted or incised retention pattern or thread 140 is disposed on the wall 106 of the cannula body 130. The inverted pattern 140 extends into the wall 106, but not through the wall 106. Consequently, the inverted pattern 140 is opposite of a typical threaded cannula in which the threads extend outwardly from the wall. In the illustrated embodiment, the inverted pattern 140 is generally helical. Consequently, the inverted pattern 140 is also referred to herein as an "inverted thread", although, as discussed below, in some embodiments, the inverted pattern 120 is not helical. In the illustrated embodiment, the inverted thread 140 is right handed, although in other embodiments, the inverted thread 140 is left handed, comprises right-handed and left-handed portions, or is not handed. An outer diameter of the inverted thread 140 is not greater than an outer diameter of the cannula body 130.

Embodiments of the cannula 100 comprise any suitable material, for example, metal, polymer, and composites thereof. In some embodiments, the cannula 100 comprises at least one of polycarbonate and polyester. In some embodiments, the cannula 100 is injection molded. In other embodiments, the cannula 100 is cast, forged, and/or machined.

A trocar comprising the retention cannula 100 comprising the inverted thread 140 exhibits improved tissue fixation and/or retention compared with an unthreaded cannula. Some embodiments of the fixation cannula 100 exhibit at least as high a tissue retention force as a typical threaded cannula. Compared with a threaded cannula, the cannula 100 exhibits reduced tissue trauma because the incision into which the cannula 100 is inserted is smaller, and an overall diameter of the inverted thread cannula 100 is smaller. Because an outer diameter of the inverted threaded portion 140 is generally the same as an outer diameter of the tip 120, advancing the inverted thread 140 through a body wall does not entail additional deformation of the tissue beyond the deformation caused by the tip 120. In contrast, advancing the threaded portion of a threaded cannula expands the size of the opening to an outer diameter of the threads, thereby increasing tissue trauma.

It is believed that the tip 130 of the cannula expands and/or stretches the tissue as the cannula 100 is advanced through the body wall. When a desired insertion depth is reached, the stretched tissue relaxes into the inverted threads 140, thereby holding or fixing the cannula 100 in place. Embodiments of the cannula 100 are inserted and/or withdrawn directly and/or rotationally.

Thus, advantageously, cannulae described herein having inverted patterns of threads can advantageously have an insertion force substantially similar to an insertion force of an unthreaded cannula having an equivalent outer diameter to the outer diameter of the cannulae with inverted thread patterns described herein. However, as tissue adjacent the cannulae can relax into the inverted threads as described above, cannulae with inverted thread patterns can have superior retention force performance in terms of retention force and sealing with adjacent tissue in the body wall in an incision site as compared with nonthreaded cannulae of equivalent outer diameters. Thus, the cannulae with inverted thread patterns can provide a relatively low insertion force, similar to that of a nonthreaded cannulae, with relatively high retention performance.

Figure 2A:
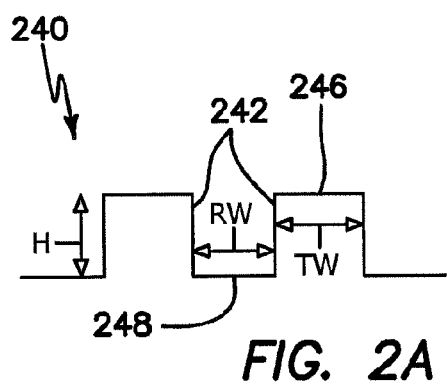
FIGS. 2A-2H illustrate cross sections of embodiments of the inverted pattern.
Figure 2B:
Figure 2C:
Figure 2D:
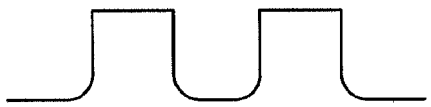
Figure 2E:
Figure 2F:
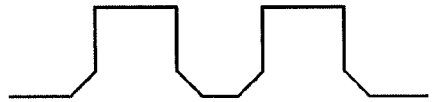
Figure 2G:
Figure 2H:
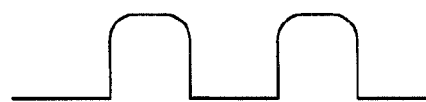

FIGS. 2A-2H illustrate cross sections of various embodiments of the inverted thread 240 for the cannulae described herein. The thread 240 comprises thread tips 246, which define an outer diameter of the cannula, thread roots 248, which define an outer diameter of the inverted pattern or inverted thread 240, and sidewalls 242 defining a channel between the thread tips 246 and the thread roots 248. With reference to FIG. 2A, in some embodiments, the threads 240 can have a generally square or rectangular cross section. With reference to FIGS. 2B-2H, in other embodiments the threads 240 have another cross section, for example, triangular, trapezoidal, circular, or a combination of cross sections as formed by varying the angles, radii, and lengths of certain features such as chamfers, fillets, and radii where edges of the thread tips 246 and sidewalls 242 and the thread roots 248 and sidewalls 242 of the inverted thread 240 meet. In some embodiments, the thread tips 246 have substantially the same width, TW, while in other embodiments, at least one thread tip 246 has a different width. In some embodiments, a width of at least one thread tip 246 is not constant. Similarly, in some embodiments, the thread roots 248 have substantially the same width, RW, while in other embodiments, at least one thread root 248 has a different width. In some embodiments, a width of at least one thread root 248 is not constant. In some embodiments, the width, TW, of the thread tips 246 is substantially equal to the width, RW of the thread roots 248, while in other embodiments, the widths RW, TW can be greater than or less than one another as desired to achieve a desired insertion force and retention performance.

In some embodiments, a height H or depth between the thread root 248 and thread tip 246 is the same over the inverted thread 240. Other embodiments comprise a plurality of heights H. Consequently, some embodiments comprise thread roots 248 at a plurality of depths and/or thread tips 246 at a plurality of heights. In some embodiments, at least one of a height of a thread tip 246 or a depth of a thread root 248 is not constant. In some embodiments, the height H or depth is the thread root 248 is not greater than about one half of a thickness of the cannula wall 106. In some embodiments, the depth is from about one third to about one half of the thickness of the cannula wall 106. For example, in some embodiments, for a cannula wall of from about 1.1 mm (about 0.045 inch) to about 1.3 mm (about 0.05 inch), the depth of thread root is from about 0.4 mm (about 0.015 inch) to about 0.5 mm (about 0.02 inch).

Also illustrated in FIGS. 2B-2H are combinations of fillets, chamfers, and radii on the thread tips 246 and thread roots 248. Embodiments of chamfers have a range of angles and/or depths. Embodiments of fillets have a range of radii, eccentricities, and/or shapes. Advantageously, by varying the geometry of the fillets, chamfers, and radii, an inverted thread pattern can be configured to be retained in a particular tissue type.

Returning to FIG. 1, embodiments of the inverted pattern 140 comprise at least one of a helical cut, a diagonal cut, and a flat cut, thereby defining the thread root. The term "cut" does not necessarily refer to the process by which the inverted pattern 140 is manufactured. For example, in some embodiments, at least a portion of the inverted pattern 140 is manufactured contemporaneously with the cannula 100, for example, by injection molding. In some embodiments, at least a portion of the inverted pattern 140 is manufactured by another method, for example, by machining and/or etching.

The embodiment of the inverted pattern 140 illustrated in FIG. 1 comprises a helical cut. Some embodiments comprise a plurality of helical cuts, angularly offset and/or longitudinally offset. Embodiments of helical cuts have varying pitches. The term "diagonal cut" refers to a portion of a helical cut that is less than a complete turn. The terms "diagonal cut" and "helical cut" are used interchangeably herein, and are also referred to as "lead sections". A flat cut extends circumferentially, either completely around a circumference or only around a portion thereof, and is also referred to as a "straight section". Some embodiments comprise sections with other shapes, for example, serpentine, zigzag, and/or longitudinal cuts. In some embodiments, one or more cuts or sections are linked end-to-end, thereby together defining a continuous groove. In some embodiments, all of the cuts or sections are linked end-to-end, thereby defining a single, continuous groove. Some embodiments of the inverted pattern 140 comprise a plurality of grooves. Some embodiments comprise intersecting grooves, for example, diamond and/or checkerboard patterns.

For example, some embodiments comprise an offset inverted thread groove pattern 140 in which deeper and shallower thread roots or grooves alternate. Some embodiments comprise a combination of inverted thread patterns 140 with different pitches and/or depths.

Some embodiments of the inverted pattern 140 further comprise at least one feature that extends above the wall of the cannula.

In some embodiments, at least a portion of the inverted pattern 140 does not completely encircle the body 130 of the cannula.

In some embodiments, the inverted thread 140 is patterned for retention in a particular tissue layer or plane, for example, fascia, muscle, skin, and/or fat. In some embodiments the inverted thread 140 comprises a plurality of regions offset longitudinally, at least one of which is patterned for retention in a particular tissue layer.

EXAMPLE 1

Figure 3:
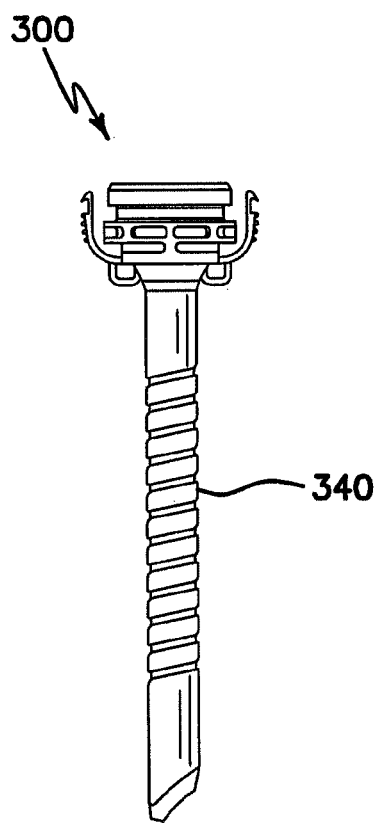
FIG. 3 is a side view of another embodiment of a cannula comprising an inverted thread.

FIG. 3 is a side view of an embodiment of a cannula 300 comprising an inverted thread 340 comprising a helical cut. A pitch of the helical cut is greater than a pitch of the helix in the embodiment illustrated in FIG. 1.

EXAMPLE 2

Figure 4:
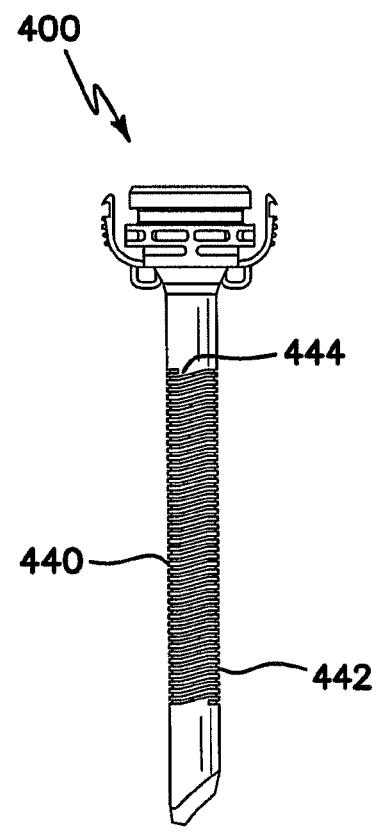
FIG. 4 is a side view of another embodiment of a cannula comprising an inverted thread.

FIG. 4 is a side view of an embodiment of a cannula 400 comprising an inverted thread 440 comprising flat cuts (straight sections) 442 and diagonal or helical cuts (lead sections) 444.

EXAMPLE 3

Figure 5:
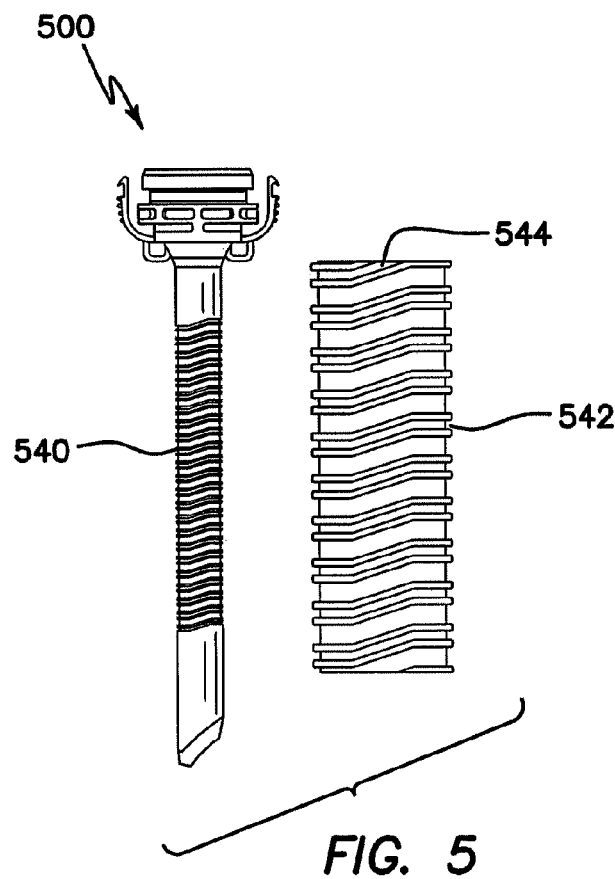
FIG. 5 is a side view of another embodiment of a cannula comprising an inverted thread.

FIG. 5 is a side view of an embodiment of a cannula 500 comprising an inverted thread 540 comprising double flat cuts (straight sections) 542 and double helical cuts (lead sections) 544. The threaded portion 540 comprises two thread root widths.

EXAMPLE 4

Figure 6:
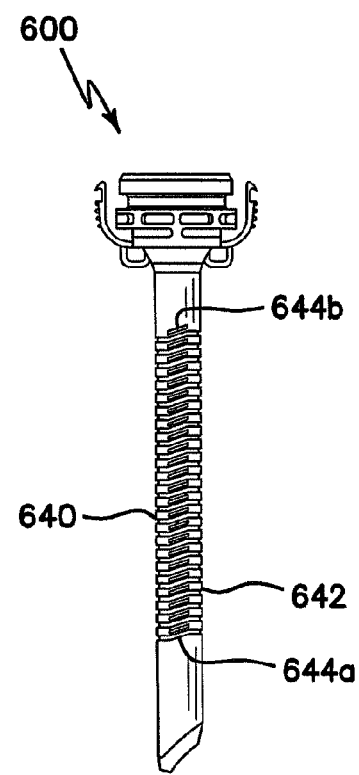
FIG. 6 is a side view of another embodiment of a cannula comprising an inverted thread.

FIG. 6 is a side view of an embodiment of a cannula 600 comprising an inverted thread 640 comprising flat cuts (straight sections) 642 and helical cuts (lead sections) 644a, which together define a continuous groove, and isolated diagonal cuts 644b disposed between adjacent helical cuts 644a on front and back sides of the cannula 600. The threaded portion 640 comprises two thread tip widths.

EXAMPLE 5

Figure 7:
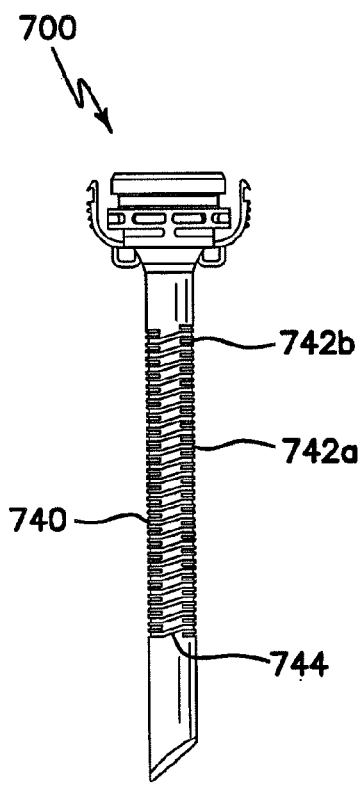
FIG. 7 is a side view of another embodiment of a cannula comprising an inverted thread.

FIG. 7 is a side view of an embodiment of a cannula 700 comprising an inverted thread 740 comprising first flat cuts (straight sections) 742a and helical cuts (lead sections) 744, which together define a continuous groove, and isolated second flat cuts 742b disposed between adjacent first flat cuts 742a on left and right sides of the cannula 700. The threaded portion 740 comprises two thread tip widths.

EXAMPLE 6

Figure 8:
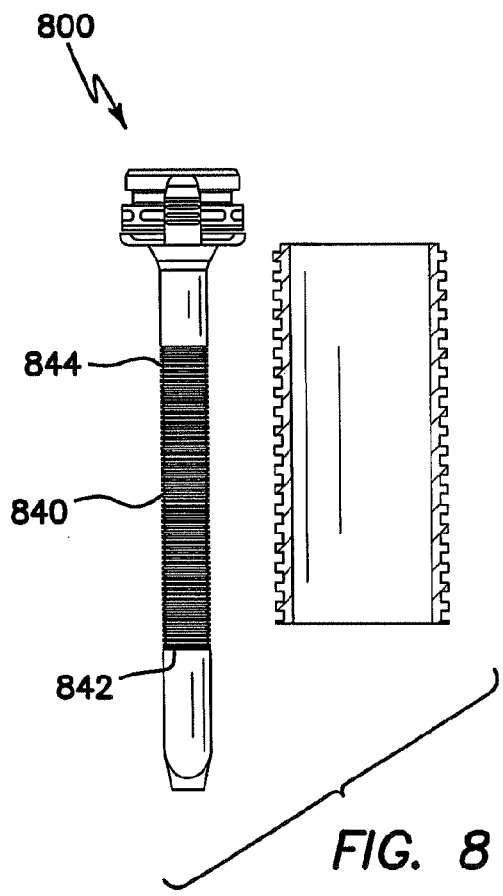
FIG. 8 is a side view of another embodiment of a cannula comprising an inverted thread.

FIG. 8 is a side view of an embodiment of a cannula 800 comprising an inverted thread 840 comprising double flat cuts (straight sections) 842 and double helical cuts (lead sections) 844. The threaded portion 840 comprises generally equal thread root and thread tip widths.

EXAMPLE 7

Figure 9A:
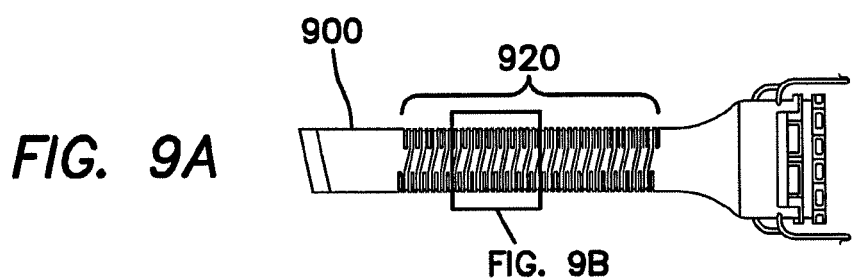
FIGS. 9A-9B illustrate a side view and a side detail view, respectively, of another embodiment of cannula comprising an inverted thread.
Figure 9B:
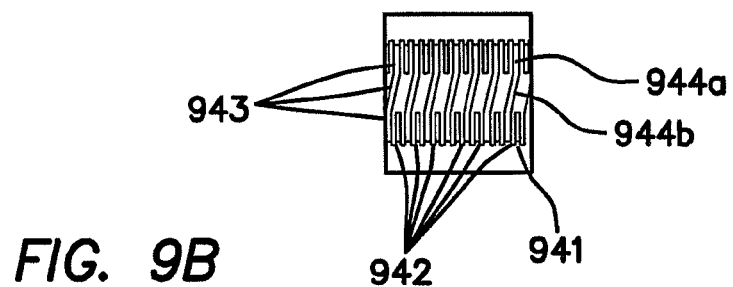

FIGS. 9A-9B are a side view and side detail view of an embodiment of a cannula 900 comprising a threaded portion 920 having an inverted pattern or thread 940 having a first plurality of thread roots 941 having first flat cuts 942 (straight sections), and a second plurality of thread roots 943 having second flat cuts (straight sections) 944a and angled cuts (lead sections) 944b, which together define a continuous groove, and positioned such that isolated first flat cuts 942 are disposed between adjacent second flat cuts 944a on left and right sides of the cannula 900. Thus, the inverted pattern of the cannula 900 are similar to that described above with respect to FIG. 7.

With continued reference to FIGS. 9A-9B a first plurality of thread roots 941 is defined by the first flat cuts 942. The first plurality of thread roots 941 extends circumferentially about a wall of the cannula 900 in a direction generally perpendicularly to a longitudinal axis of the cannula 900. In some embodiments, the first plurality of thread roots 941 can be non-continuous, extending circumferentially about the cannula wall about an arc segment defining an angle less than 360 degrees. In the illustrated embodiment, the first plurality of thread roots extends circumferentially about an arc segment defining an angle less than approximately 180 degrees.

With continued reference to FIGS. 9A-9B, the second plurality of thread roots 943 has a plurality of second flat cuts 944a or retention segments that each extend circumferentially about the cannula wall perpendicularly to the longitudinal axis of the cannula 900 and a plurality of helical or angled cuts 944b or flow channels each extending circumferentially about the cannula wall transverse to the longitudinal axis. In the illustrated embodiment, the retention segments are joined to adjacent flow channels to define a continuous channel extending peripherally about the cannula 900 from a proximal end of the threaded portion 920 to a distal end of the threaded portion 920. Advantageously, the transverse extent of the flow channels can allow for fluid to be vented or evacuated in a proximal direction during insertion of the cannula, thus facilitating insertion of the cannula.

With continued reference to FIGS. 9A-9B, in some embodiments, each retention segment of the second plurality of thread roots 943 is spaced from an adjacent retention segment by at least one of the thread roots of the first plurality of thread roots 941. In some embodiments, each retention segment is spaced from an adjacent retention segment by one of the thread roots of the first plurality of thread roots 941. Thus, in the illustrated embodiment, from a distal end to a proximal end of the threaded portion 920, the inverted pattern can take the form of a first plurality thread roots 941 extending perpendicularly to the longitudinal axis of the cannula and having an arc length of less than 180 degrees about the cannula alternating with retention segments of the second plurality of thread roots 943 extending generally perpendicularly to the longitudinal axis of the cannula. The retention segments are joined to one another by flow channels of the second plurality of thread roots 943 extending transverse to the longitudinal axis of the cannula.

Figure 10A:
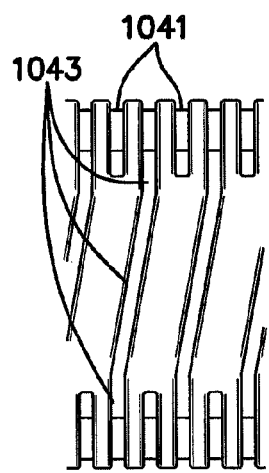
FIGS. 10A-10F illustrate side views of other embodiments of cannulae comprising an inverted thread.
Figure 10B:
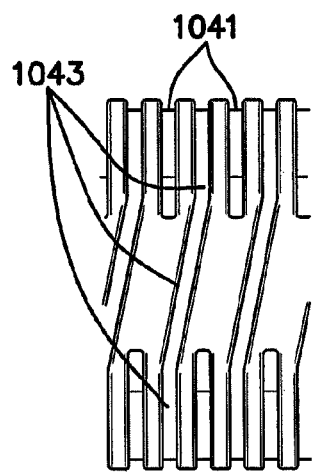
Figure 10C:
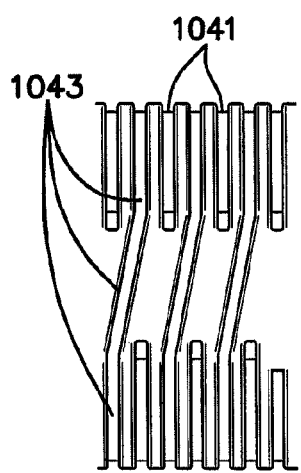
Figure 10D:
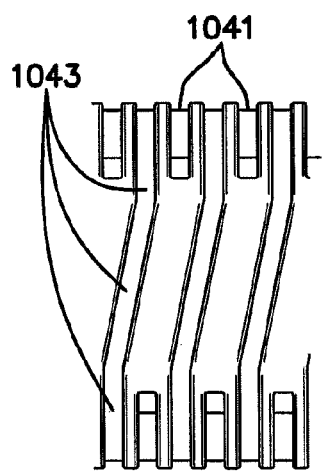
Figure 10E:
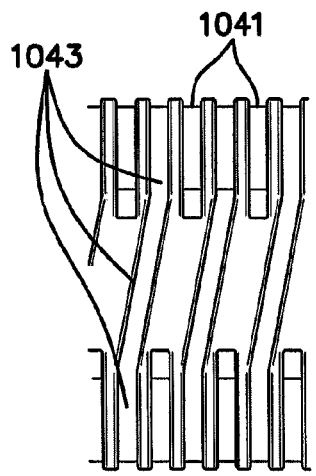

FIGS. 10A-10F illustrate other embodiments of trocar having similarities to the embodiments of FIGS. 9A-9B. For example, the trocars illustrated in FIGS. 10A-10E have a first plurality of thread roots 1041 and a second plurality of thread roots 1043 arranged substantially similar to the first and second pluralities of thread roots of FIGS. 9A and 9B. However, FIGS. 10A-10E illustrate embodiments having variations in the widths of the thread roots and thread tips as may be desired to configure a trocar for insertion in a particular tissue type. For example, in some embodiments, the thread tip width can be substantially equal to the thread root width (FIG. 10A), in other embodiments, the thread tip width can be larger than the thread root width (FIGS. 10B, 10C), and in other embodiments, the thread tip width can be smaller than the thread root width (FIGS. 10D, 10E).

With continued reference to FIGS. 10A-10E, in some embodiments, the arc length of the first plurality of thread roots 1041 can be varied from significantly less than 180 degrees (FIG. 10A) to approaching 180 degrees (FIG. 10C). In the illustrated embodiments, the first plurality of thread roots 1041 does not intersect the flow channels of the second plurality of thread roots 1043. Other embodiments can include intersecting thread roots.

Figure 10F:
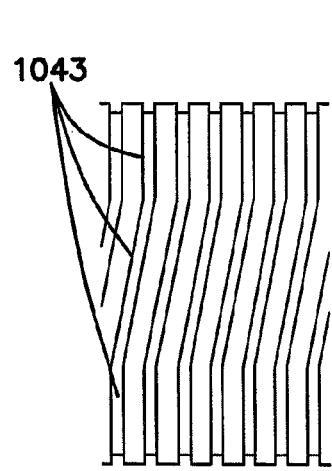

With reference to FIG. 10F, an embodiment of cannula is shown that is similar to the embodiments of FIGS. 9A-9B. However, as illustrated in FIG. 10F, the cannula comprises a continuous thread 1043 or groove defined by a plurality of flat cuts or retention segments that each extend circumferentially about the cannula wall perpendicularly to the longitudinal axis of the cannula and a plurality of cuts or flow channels each extending circumferentially about the cannula wall transverse to the longitudinal axis. Thus, in the embodiment of FIG. 10F, unlike the cannulae illustrated in FIGS. 9A, 9B, and 10A-10E, there are no additional flat cuts separating adjacent flat cuts of the continuous groove.

Figure 11A:
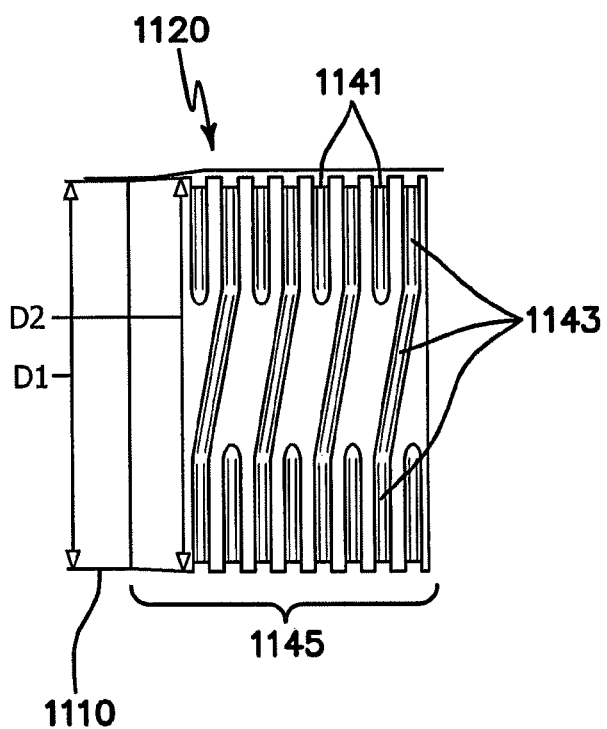
FIG. 11A illustrates a side view of another embodiment of cannula comprising an inverted thread.
Figure 11B:
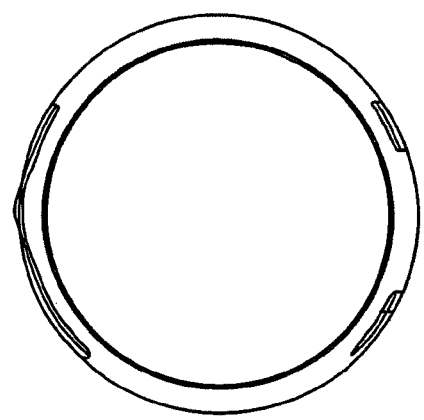
FIG. 11B illustrates a cross-sectional view of the cannula of FIG. 11A.

With reference to FIGS. 11A-11B, another embodiment of cannula is illustrated having similarities to the cannulae of FIGS. 9A-9B and 10A-10E. In the illustrated embodiment, the cannula has a first plurality of thread roots 1141 and a second plurality of thread roots 1143 substantially as described above with respect to cannulae of FIGS. 9A-9B. However, the embodiment of cannula illustrated in FIG. 11A-11B can include a retention region 1145 having a relatively high cannula outer diameter D2 over the threaded portion 1120 of the cannula as compared to the outer diameter D1 of the remainder of the cannula, such as the distal end 1110 or tip. In some embodiments, the retention region 1145 can include a corresponding region of relatively high cannula wall thickness, while in other embodiments, the outer diameter D2 of the cannula can be increased at the retention region 1145 while the wall thickness remains substantially constant over a length of the cannula. Such a region having a relatively high outer diameter D2 as compared to the outer diameter D1 of the cannula at the distal end 1110 can advantageously provide enhanced retention at the incision site while having relatively low insertion force. In some embodiments, the outer diameter D2 of the retention region 1145 of the cannula can be approximately 0.005 inches (or approximately 0.127 mm) larger than the outer diameter D1 of the non-threaded portion of the cannula, such as the distal end 1110.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A trocar comprising:
   a retention cannula comprising:
      a proximal end, a distal end, and a longitudinal axis;
      a tip disposed at the distal end of the cannula,
      a cannula body between the proximal end of the cannula and the tip, the cannula body having a cannula wall defining a lumen extending between the proximal end and the distal end; and
      an inverted, tissue retention pattern having a thread root depth extending into the wall of the cannula body, the inverted tissue retention pattern defined by a first continuous groove having alternating flat cuts extending generally perpendicularly to the longitudinal axis and helical cuts extending transverse to the longitudinal axis and a second continuous groove having alternating flat cuts extending generally perpendicularly to the longitudinal axis and helical cuts extending transverse to the longitudinal axis;
      wherein an outer diameter of the inverted tissue retention pattern is not greater than an outer diameter of the cannula body.

2. The trocar of claim 1, wherein the first continuous groove has a first thread root width and the second continuous groove has a second thread root width different from the first thread root width.

3. The trocar of claim 1, wherein the first continuous groove comprises thread tips extending to the outer diameter of the cannula body, thread roots defining the outer diameter of the inverted pattern, and sidewalls defining a channel between the thread tips and the thread roots.

4. The trocar of claim 3, wherein the first continuous groove has a generally rectangular cross-sectional profile.

5. The trocar of claim 1, wherein the retention cannula is comprised of at least one of a polycarbonate material and a polyester material.

6. A trocar comprising:
   a retention cannula comprising:
      a proximal end, a distal end, and a longitudinal axis;
      a tip disposed at the distal end of the cannula,
      a cannula body between the proximal end of the cannula and the tip, the cannula body having a cannula wall defining a lumen extending between the proximal end and the distal end; and
      an inverted, tissue retention pattern having a thread root depth extending into the cannula wall of the cannula body, the inverted tissue retention pattern comprising a plurality of retention segments each extending generally perpendicularly to the longitudinal axis, and a plurality of flow channels each extending transverse to the longitudinal axis;
      wherein an outer diameter of the inverted tissue retention pattern is not greater than an outer diameter of the cannula body.

7. The trocar of claim 6, wherein each of the plurality of retention segments is joined end-to-end to an adjacent one of the flow channels such that the inverted tissue retention pattern comprises a continuous groove.

8. The trocar of claim 7, wherein the inverted tissue retention pattern further comprises a second plurality of retention segments disposed between adjacent retention segments of the continuous groove.

9. The trocar of claim 7, wherein the inverted tissue retention pattern further comprises a second plurality of flow channels disposed between adjacent flow channels of the continuous groove.

10. The trocar of claim 6, wherein the cannula wall has a thickness and wherein the thread root depth of the inverted tissue retention pattern is from about one-third to about one-half of the thickness of the cannula wall.

11. The trocar of claim 6, wherein the cannula wall comprises a region of relatively high wall thickness and wherein the inverted tissue retention pattern is disposed in the region of relatively high thickness.

12. A trocar comprising:
   a retention cannula comprising:
      a proximal end, a distal end, and a longitudinal axis;
      a tip disposed at the distal end of the cannula, the tip defining an angled and beveled distal end;
      a generally cylindrical cannula body between the proximal end of the cannula and the tip, the cannula body having a cannula wall defining a lumen extending between the proximal end and the distal end;
      a bell-shaped region at the proximal end, the bell-shaped region couplable to a trocar seal housing; and
      an inverted, tissue retention pattern extending into the cannula wall, the inverted tissue retention pattern comprising a continuous groove defined by a plurality of circumferential groove segments each extending generally perpendicularly to the longitudinal axis, alternating with a plurality of helical groove segments each extending transverse to the longitudinal axis;
      wherein an outer diameter of the inverted tissue retention pattern is not greater than an outer diameter of the cannula body.

13. The trocar of claim 12, wherein the retention cannula comprises at least one of a polycarbonate and a polyester material.

14. The trocar of claim 12, wherein the inverted tissue retention pattern comprises at least one of a chamfer, a fillet, and a radiused edge.

15. The trocar of claim 12, wherein the inverted tissue retention pattern further comprises a plurality of isolated non-continuous segments extending into the cannula wall of the cannula body.

16. The trocar of claim 15, wherein each of the isolated non-continuous segments extends generally perpendicularly to the longitudinal axis.

17. The trocar of claim 15, wherein each of the isolated non-continuous segments extends transversely to the longitudinal axis.

* * * * *